(12) United States Patent
Hamada

(10) Patent No.: US 8,740,798 B2
(45) Date of Patent: Jun. 3, 2014

(54) THREE-DIMENSIONAL ULTRASONIC DIAGNOSIS APPARATUS

(75) Inventor: Kenji Hamada, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 262 days.

(21) Appl. No.: 12/822,692

(22) Filed: Jun. 24, 2010

(65) Prior Publication Data

US 2010/0331701 A1 Dec. 30, 2010

(30) Foreign Application Priority Data

Jun. 25, 2009 (JP) ................................. 2009-151140

(51) Int. Cl.
*A61B 8/06* (2006.01)

(52) U.S. Cl.
USPC ........... 600/454; 600/437; 600/443; 600/447; 600/446; 382/128

(58) Field of Classification Search
USPC ........... 600/437, 413, 443, 447, 454; 382/128
See application file for complete search history.

(56) References Cited

U.S. PATENT DOCUMENTS

| | | | |
|---|---|---|---|
| 5,435,303 A * | 7/1995 | Bernstein et al. .............. | 600/413 |
| 5,782,769 A | 7/1998 | Hwang et al. | |
| 6,245,017 B1 * | 6/2001 | Hashimoto et al. ........... | 600/447 |
| 6,966,878 B2 | 11/2005 | Schoisswohl et al. | |
| RE38,971 E * | 2/2006 | Kamiyama .................... | 600/443 |
| 2004/0081270 A1 * | 4/2004 | Heuscher .......................... | 378/4 |
| 2006/0078182 A1 * | 4/2006 | Zwirn et al. ................... | 382/128 |
| 2010/0036247 A1 * | 2/2010 | Yamamoto et al. ........... | 600/443 |
| 2010/0036248 A1 * | 2/2010 | Chouno ......................... | 600/443 |
| 2010/0234730 A1 * | 9/2010 | Fukuzawa et al. ............ | 600/443 |
| 2010/0331701 A1 * | 12/2010 | Hamada ......................... | 600/454 |
| 2012/0078097 A1 * | 3/2012 | Wang et al. ................... | 600/437 |

FOREIGN PATENT DOCUMENTS

| | | |
|---|---|---|
| JP | 2005-74225 | 3/2005 |
| JP | 2009-22342 | 2/2009 |

* cited by examiner

*Primary Examiner* — Baisakhi Roy
(74) *Attorney, Agent, or Firm* — Oblon, Spivak, McClelland, Maier & Neustadt, L.L.P.

(57) ABSTRACT

According to one embodiment, an ultrasonic diagnosis apparatus includes an ultrasonic probe and an ultrasonic scanning unit configured to repeatedly scan an interior of an subject with an ultrasonic wave via the ultrasonic probe and repeatedly acquire echo signals. An image generation unit generates data of blood flow images based on the echo signals. An interpolation processing unit identifies at least one pixel in which clutter components occupy the majority of the pixel value, and to interpolate a pixel value of the identified pixel based on pixel values of at least two other blood flow images corresponding to a substantially same cardiac phase as that of the blood flow image including the identified pixel.

19 Claims, 5 Drawing Sheets

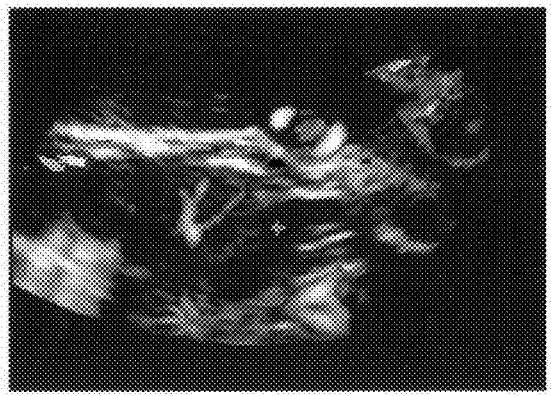
F I G. 6
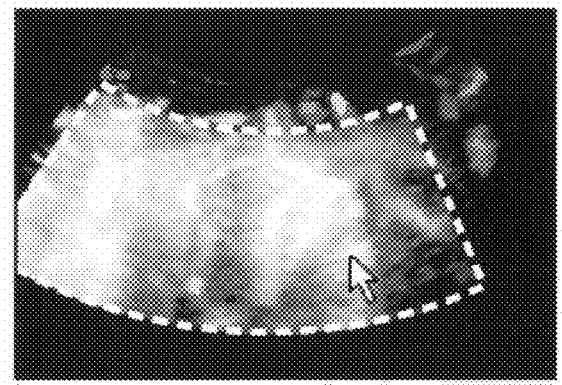
F I G. 7
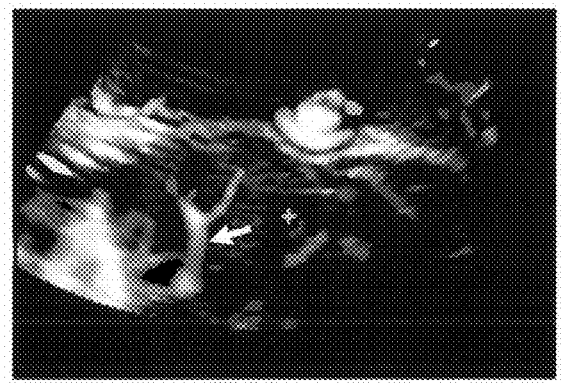
F I G. 8

THREE-DIMENSIONAL ULTRASONIC DIAGNOSIS APPARATUS

CROSS-REFERENCE TO RELATED APPLICATIONS

This application is based upon and claims the benefit of priority from Japanese Patent Application No. 2009-151140, filed Jun. 25, 2009; the entire contents of which are incorporated herein by reference.

FIELD

Embodiments described herein relate generally to a three-dimensional ultrasonic diagnosis apparatus.

BACKGROUND

An ultrasonic diagnosis apparatus which equips a color Doppler mode displays the two-dimensional distributions of velocity, power, and variance based on a Doppler signal concerning a moving target such as a blood flow. This apparatus can also display a three-dimensional blood flow image or blood flow information at an arbitrary cross-sectional position.

When visualizing a pulsating blood flow in, e.g., a heart or artery, its cycle is analyzed, and received rasters are rearranged, thereby three-dimensionally displaying the cardiac motion for one heartbeat.

Some recent ultrasonic diagnosis apparatuses can detect the blood flow of a fetus to diagnose the fetal developmental state or fetal diseases. A color Doppler method uses a clutter filter which reduces tissue components (clutter components) of a Doppler signal.

The clutter filter reduces low-frequency components of a doppler signal. Many clutter components are reduced by the clutter filter. However, the clutter filter passes the clutter components of quickly moving tissues together with the blood flow components. The clutter components that have passed through the clutter filter appear as clutter noise which makes it difficult to clearly visualize the blood flow of a fetus or the like.

BRIEF DESCRIPTION OF THE DRAWINGS

FIG. 6 is a view showing the (N−1)th image so as to explain clutter region calculation processing of a clutter region calculation unit in FIG. 1;

FIG. 7 is a view showing the Nth image so as to explain clutter region calculation processing of the clutter region calculation unit in FIG. 1; and FIG. 8 is a view showing the (N+1)th image so as to explain clutter region calculation processing of the clutter region calculation unit in FIG. 1.

DETAILED DESCRIPTION

In general, according to one embodiment, an ultrasonic diagnosis apparatus includes an ultrasonic probe and an ultrasonic scanning unit configured to repeatedly scan an interior of an subject with an ultrasonic wave via the ultrasonic probe and repeatedly acquire echo signals. An image generation unit generates data of blood flow images based on the echo signals. An interpolation processing unit identifies at least one pixel in which clutter components occupy the majority of the pixel value, and to interpolate a pixel value of the identified pixel based on pixel values of at least two other blood flow images corresponding to a substantially same cardiac phase as that of the blood flow image including the identified pixel.

Clutter noise has low time continuity. In other words, clutter noise has a high transitory characteristic. Clutter noise largely varies over time. On the other hand, a blood flow component has high time continuity. In this embodiment, clutter noise is effectively reduced using the characteristic difference between these two types of signal components. A plurality of blood flow images are grouped for each cardiac phase. A plurality of blood flow images of the same group are arranged in accordance with the scanning time. This discretizes the clutter noise both spatially and temporally. That is, the low time continuity of clutter noise is enhanced by the grouping and arranging. Blood flow images containing clutter noise are located between blood flow images without clutter noise. Hence, filtering processing efficiently reduces clutter noise components.

Figure 1:
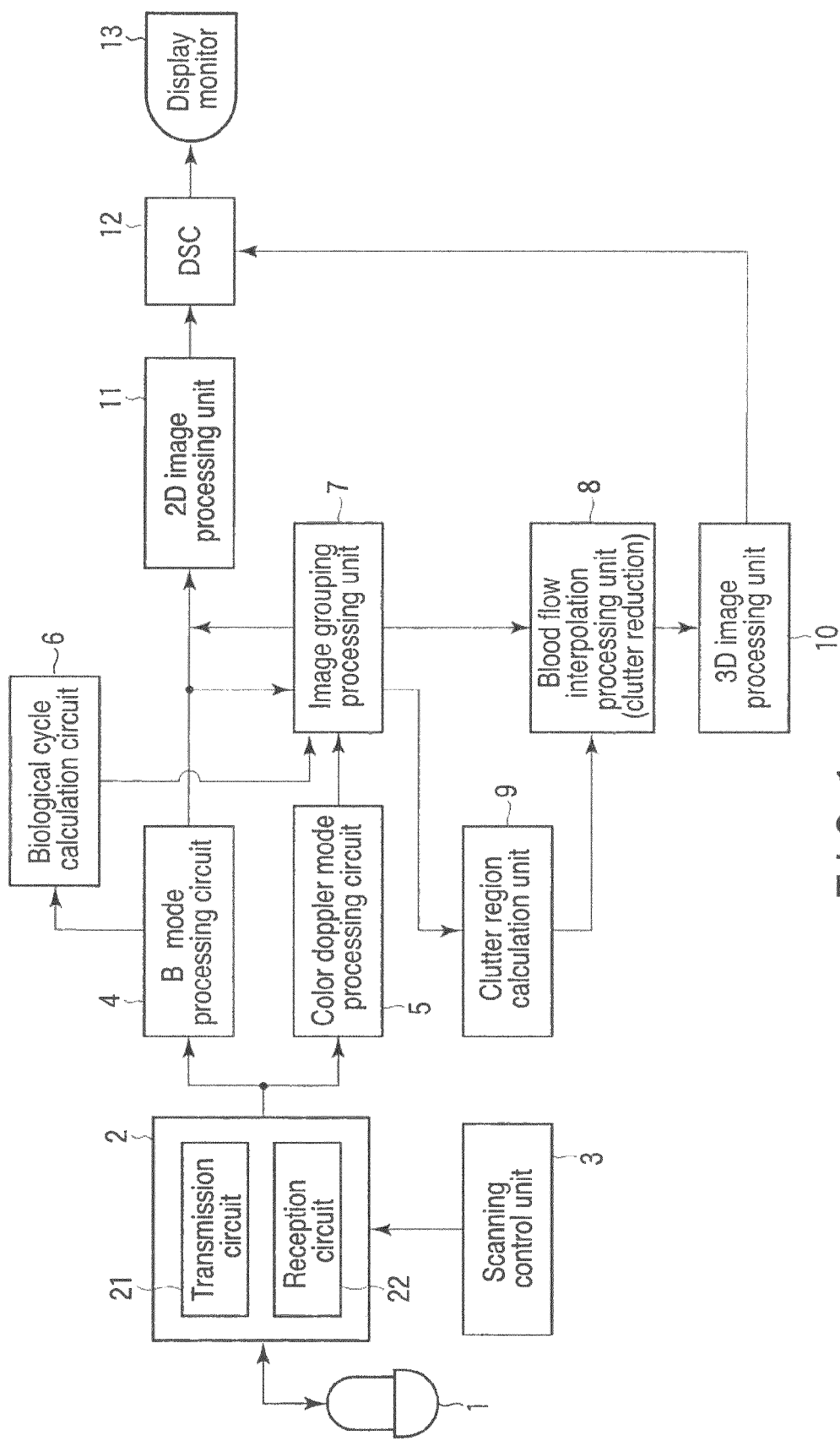
FIG. 1 is a block diagram showing the arrangement of an ultrasonic diagnosis apparatus according to the embodiment.

FIG. 1 shows the arrangement of an ultrasonic diagnosis apparatus according to the embodiment. The ultrasonic diagnosis apparatus has an ultrasonic probe 1. The ultrasonic probe 1 includes a plurality of piezoelectric vibrators which are one-dimensionally arrayed to generate an ultrasonic wave upon receiving a driving signal from a transmission circuit 21 of a transmission/reception unit 2 and convert the wave reflected by an object into an electrical signal, a matching layer provided on the piezoelectric vibrators, and a backing material for preventing ultrasonic wave propagation from the piezoelectric vibrators to the rear. When the ultrasonic probe 1 transmits an ultrasonic wave to an subject, the transmitted ultrasonic wave is successively reflected by the discontinuity surfaces of acoustic impedance of internal tissues, and received by the ultrasonic probe 1 as an echo signal. The amplitude of the echo signal depends on the difference of acoustic impedance on the discontinuity surfaces that have reflected the ultrasonic wave. If the transmitted ultrasonic pulse is reflected by a moving blood flow or cardiac wall surface, the echo signal suffers frequency shift depending on the velocity component of the moving body in the ultrasonic wave transmission direction due to the Doppler effect.

A reception circuit 22 includes a preamplifier, A/D converter, reception delay unit, adder, and the like. The preamplifier amplifies the echo signal received via the ultrasonic probe 1 for each channel. The reception delay unit gives a delay time necessary for determining the reception directivity to the amplified echo signal. The adder then performs addition processing. With this addition, reflected components from a direction corresponding to the reception directivity of the echo signal are enhanced so that a total beam of ultrasonic transmission/reception is formed based on the reception directivity and transmission directivity.

Under the control of a scanning control unit 3, the transmission circuit 21 and the reception circuit 22 repeat ultrasonic scanning of a two-dimensional cross section. During the repetitive ultrasonic scanning, the technician slowly moves the ultrasonic probe 1 on the mother's body surface corresponding to, for example, the heart of a fetus, thereby scanning a three-dimensional region including the fetal heart. This scanning is called three-dimensional scanning. Note that in this embodiment, B-mode scanning and color Doppler mode scanning are alternately repeated.

A B-mode processing circuit 4 receives the echo signal from the reception circuit 22, and performs logarithmic amplification, envelope detection, and the like, thereby generating so-called B-mode image data (form image data) which expresses a signal strength as a luminance level so as to reflect the internal structure as a change in luminance. A two-dimensional (2D) image processing unit 11 converts the two-dimensional display target image into a luminance image or color image.

A color Doppler mode processing circuit 5 extracts the echo components of blood flows, tissues, and contrast medium by the Doppler effect, and generates so-called color flow mapping data (blood flow image data) that expresses the spatial distributions of average velocity, variance, power, and the like in color.

A biological cycle calculation circuit 6 extracts a target organ which periodically changes its form, i.e., the cardiac muscle contour of the fetus heart from the form image (B-mode image) data, and identifies the cardiac phase of each form image during scanning based on the time-rate change of the cardiac muscle contour. The cardiac phase of each image during scanning may be measured using an electrocardiograph in place of the biological cycle calculation circuit 6. Each cardiac phase identified by the biological cycle calculation circuit 6 is supplied to an image grouping processing unit 7 together with corresponding blood flow image data.

In FIG. 1, B-mode data is used in the biological cycle calculating, however the color Doppler-mode data may is used in the biological cycle calculating.

The image grouping processing unit 7 divides the plurality of blood flow images generated by the color Doppler mode processing circuit 5 into a plurality of groups corresponding to a plurality of cardiac phases in accordance with the scanning timing. The image grouping processing unit 7 arranges a plurality of blood flow images of each group in accordance with the scanning timing. Blood flow images belonging to the same group result from echo signals acquired by scanning in the same cardiac phase. Blood flow images of the same group belong to different cardiac cycles. The cardiac cycle indicates a time from, for example, a given R wave to the next R wave of an electrocardiographic wave. A cardiac phase indicates a position within the cardiac cycle. Typically, the cardiac cycle is divided into 100 equal intervals, and each position in the cardiac cycle is expressed as percentage.

A clutter region calculation unit 9 compares the pixel value of each blood flow image with a threshold predetermined mainly according to the clutter noise level of the mother body, and specifies a region (clutter region candidate) where pixels having pixel values larger than the threshold (a pixel in which clutter components occupy the majority of a pixel value) are connected to form a single lump. The clutter region calculation unit 9 compares the volume or area of the specified clutter region candidate with a threshold predetermined to detect a region that requires interpolation processing because its size spatially impairs visual recognition of a blood flow region. A clutter region candidate having a volume or area larger than the threshold is determined as an interpolation target clutter region.

A blood flow interpolation processing unit 8 replaces the pixel values in the interpolation target clutter region identified by the clutter region calculation unit 9 with values calculated from the pixel values of blood flow images belonging to the same group. More specifically, the blood flow interpolation processing unit 8 interpolates the pixel values in the interpolation target clutter region using the pixel values of corresponding pixels of two blood flow images which are in a cardiac phase at almost the same scanning timing as that of the blood flow image including the interpolation target pixels and also in cardiac cycles before and after the blood flow image including the interpolation target pixels. The interpolation processing may be performed based on four or more blood flow images obtained in four or more cardiac cycles in the vicinity of the cardiac cycle corresponding to the interpolation target blood flow image.

A three-dimensional (3D) image processing unit 10 generates volume data or an arbitrary cross section image (MPR) from a plurality of blood flow image data at different scanning positions of three-dimensional scanning, including the blood flow image interpolated by the blood flow interpolation processing unit 8.

A digital scan converter (DSC) 12 converts the form image data generated by the two-dimensional (2D) image processing unit 11 and the volume data or cross section image data generated by the 3D image processing unit 10 into a video scanning scheme corresponding to a monitor 13, and outputs the image data.

Figure 2A:
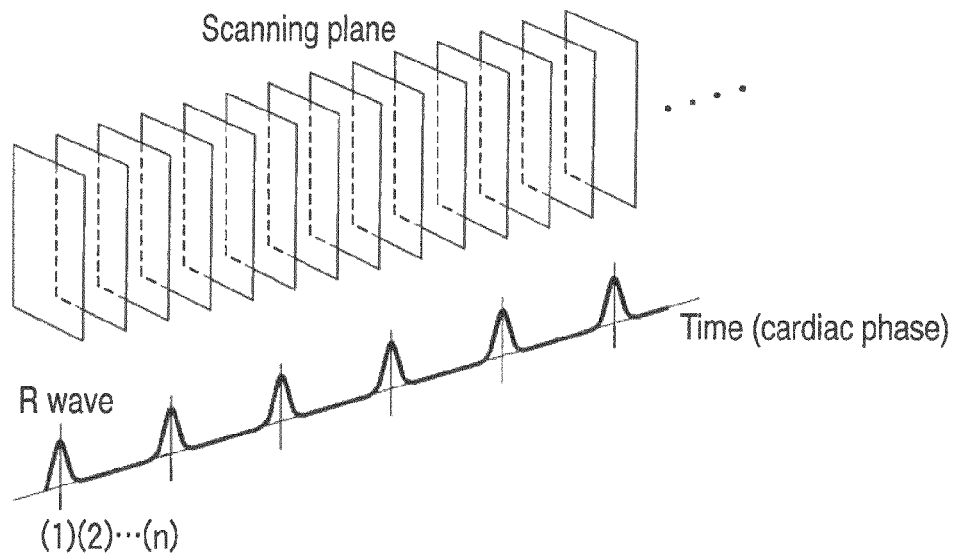
FIGS. 2A and 2B are diagrams showing blood flow image grouping of an image grouping processing unit in FIG. 1.

The operation of the embodiment will be described next. In this embodiment, as shown in FIG. 2A, under the control of the scanning control unit 3, the transmission circuit 21 and the reception circuit 22 repeat ultrasonic scanning of a two-dimensional cross section. Simultaneously, the technician slowly moves the probe 1 on the mother's body surface corresponding to, for example, the heart of a fetus. This scanning is generally called three-dimensional scanning. The three-dimensional scanning need not always be done by a manual method. It may be performed by a mechanical method of mechanically swinging a probe having a plurality of piezoelectric vibrators arrayed one-dimensionally, or an electronic method of electronically swinging the scanning surface using a probe having a plurality of piezoelectric vibrators arrayed two-dimensionally.

In this embodiment, B-mode scanning and color Doppler mode scanning are alternately repeated. In B-mode scanning, the biological cycle calculation circuit 6 identifies the cardiac phase of the fetus based on the form change of the heart on the B-mode image. Pixels in the cardiac muscle region of the fetus are extracted based on a corresponding threshold. The size of the region can be identified relatively accurately from a certain range concerning a size expected of the heart of a fetus. Since the heart pulsates, its form periodically changes, as a matter of course. Hence, the scanning timing of each B-mode image can be specified as a cardiac phase based on the form change. Since B-mode scanning and color Doppler mode scanning are alternately repeated, the cardiac phase of a scanning timing of a blood flow image is almost equivalent to the cardiac phase in B-mode scanning immediately before (or immediately after) color Doppler mode scanning.

Figure 2B:
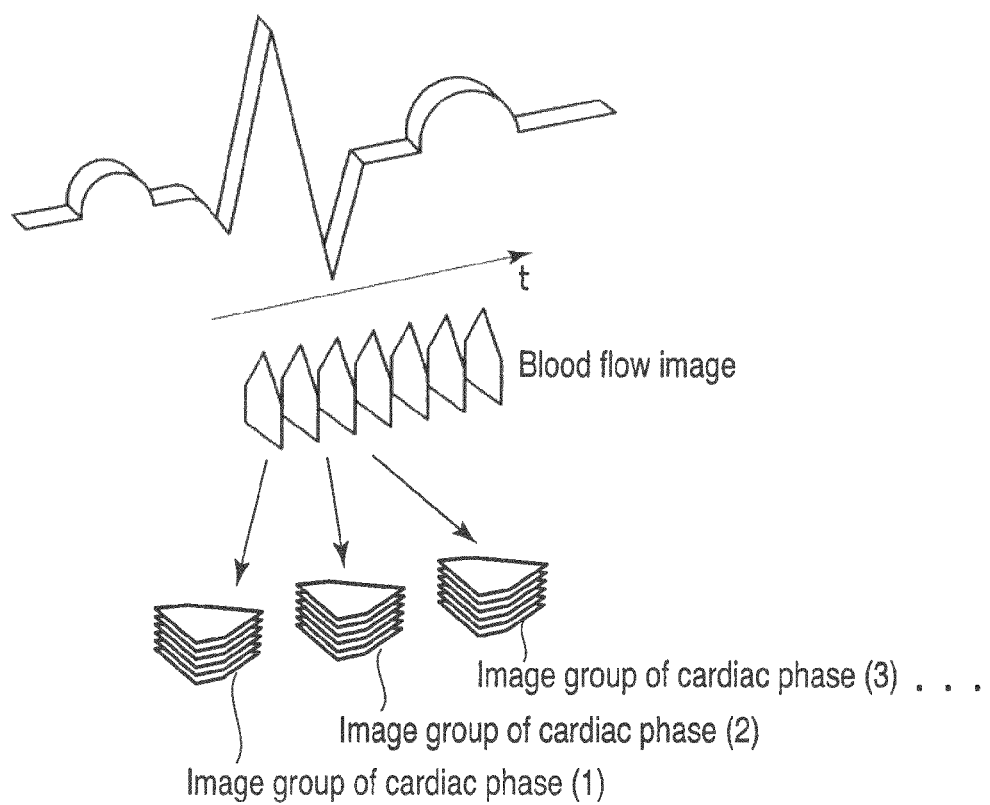

A plurality of blood flow images in which the cardiac phases of the fetus are specified by the biological cycle calculation circuit 6 are put into groups corresponding to the cardiac phases by the image grouping processing unit 7 in accordance with the scanning timing. That is, as shown in FIG. 2B, the plurality of blood flow images are classified into a plurality of blood flow image groups in accordance with the cardiac phase of the heart of the fetus, and arrayed for each blood flow image group in correspondence with the scanning timing.

Next, the clutter region calculation unit 9 compares each pixel value (one of the velocity, variance, and power) of each blood flow image with a threshold predetermined in accordance with the clutter noise level. A region where pixels having pixel values larger than the threshold (pixels in which clutter elements occupy the majority of a pixel value) are connected to form a single lump is specified as a clutter region candidate. The volume or area of the specified clutter region candidate is compared with a predetermined threshold. A clutter region candidate having a volume or area larger than the threshold is identified as an interpolation target clutter region. This is because a small clutter region does not impair visual recognition of a blood flow region, whereas a clutter region candidate that is large to some extent impairs visual recognition of a blood flow region.

Figure 5:
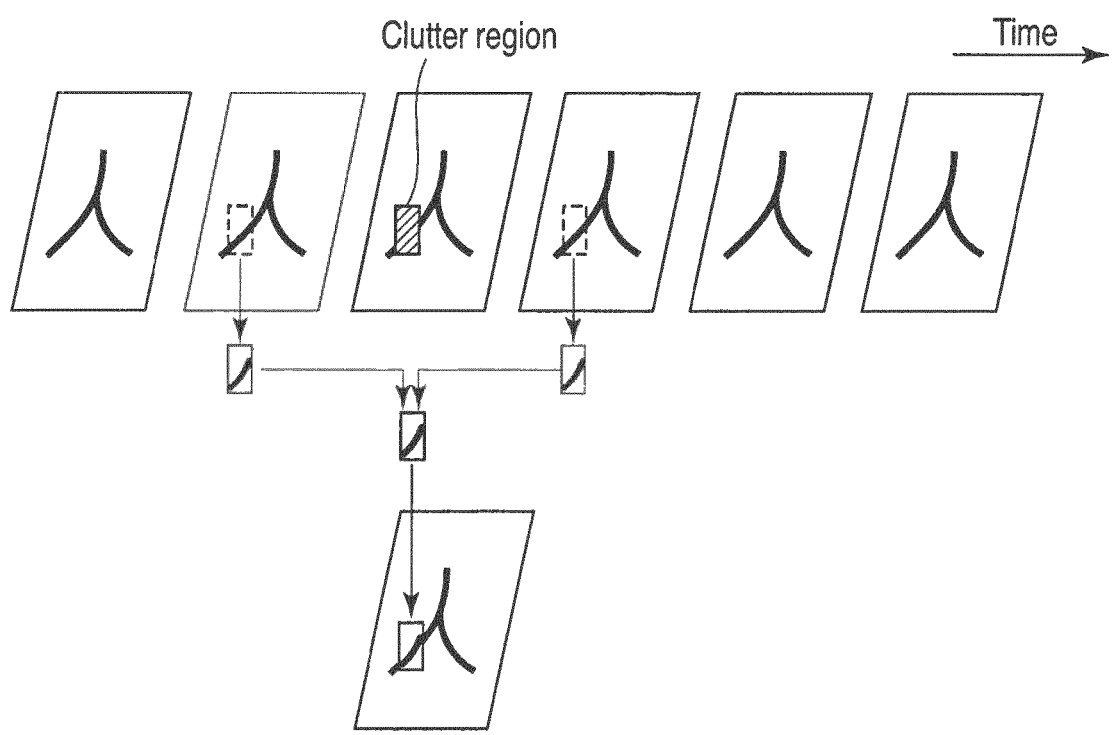
FIG. 5 is a view for explaining interpolation processing of a blood flow interpolation processing unit in FIG. 1.

As shown in FIG. 5, the blood flow interpolation processing unit 8 replaces the pixel values of pixels in the identified clutter region with interpolation values calculated from the pixel values of pixels at the same positions in the immediately preceding and succeeding blood flow images adjacent to the interpolation target blood flow image in the array of the image group including the interpolation target blood flow image. That is, the pixel values of the interpolation target pixels are replaced with interpolation values calculated from the pixel values of corresponding pixels of two blood flow images which are in a cardiac phase at almost the same scanning timing as that of the interpolation target blood flow image and at the scanning timings before and after the blood flow image including the interpolation target clutter region.

A pixel value ($S_{x,y,z}$) in the interpolation target blood flow image is calculated as the average value of pixel values ($S_{x,y,z-1}$) and ($S_{x,y,z+1}$) of pixels at the same position in the immediately preceding and succeeding blood flow images by $$S_{x,y,z}=(S_{x,y,z-1}+S_{x,y,z+1})/2$$

Note that the average value of two, immediately preceding and succeeding frames is calculated as a typical example. However, the average value of three, four, or more frames may be calculated.

Figure 3:
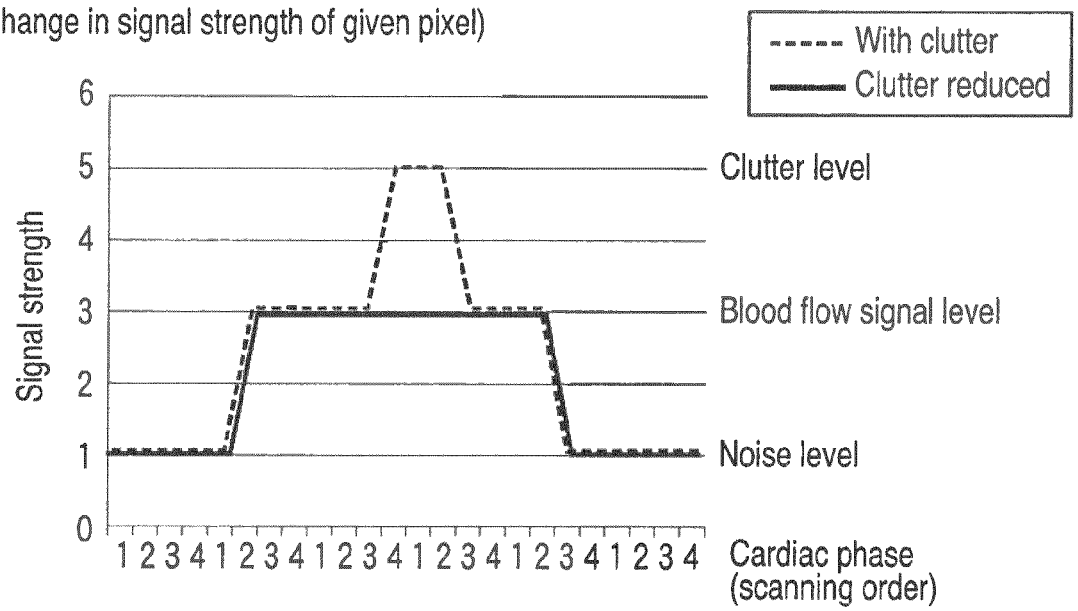
FIG. 3 is a graph schematically showing a pixel value change in the scanning order according to the embodiment.
Figure 4:
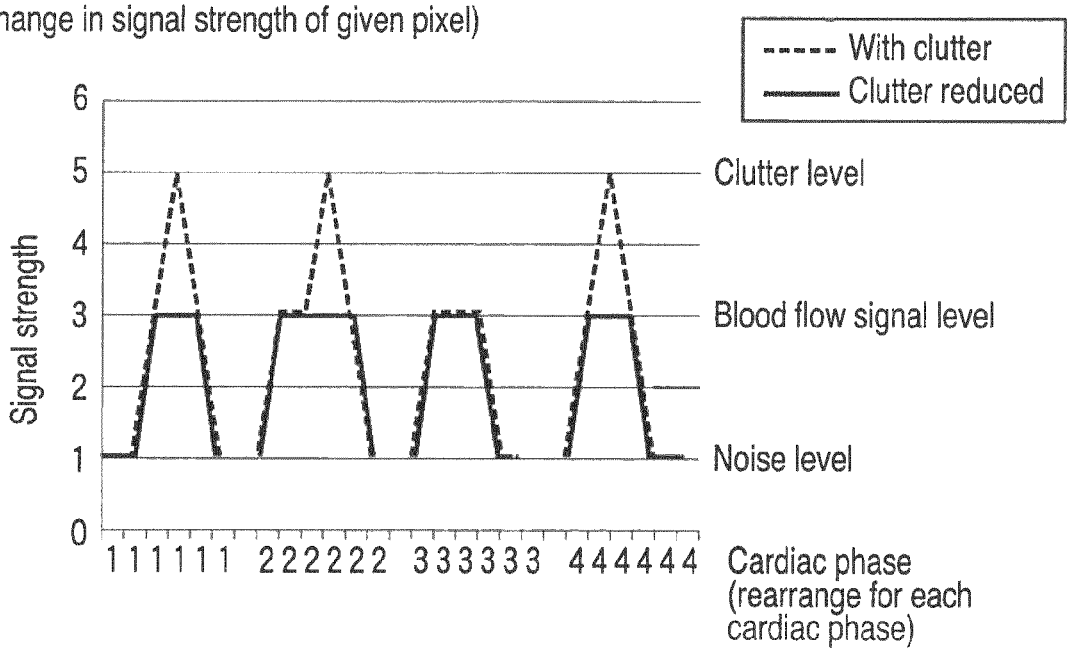
FIG. 4 is a graph schematically showing a pixel value change in each cardiac phase according to the embodiment.

This allows effective removal of the clutter region. As shown in FIG. 3, clutter noise generally has low time continuity. In other words, clutter noise has high transitory tendency. On the other hand, a blood flow component tends to have high time continuity. As in the embodiment, when the blood flow images are rearranged for each cardiac phase, as shown in FIG. 4, the blood flow images containing clutter noise are dispersed both spatially and temporally, so clutter noise typically appears only in one frame of each group and hardly appears in preceding and succeeding frames. Additionally, an interpolation value calculated from blood flow images of the same cardiac phase never largely deviates from the true value. It is therefore possible to effectively reduce the clutter noise components and also perform interpolation using reliable interpolation values. Localizing interpolation for a clutter region that has great influence to conceal the blood flow makes it possible to reduce the load of interpolation processing and directly use the pixel values of a blood flow portion without clutter components or with a few clutter components. FIG. 6 shows an original blood flow image. FIG. 7 shows an identified clutter region indicated by a broken line. As is apparent from FIG. 8, interpolation processing of this embodiment enables recovery of a blood flow portion (indicated by an arrow) that has been invisible due to clutter.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus comprising:
   an ultrasonic probe;
   an ultrasonic configured scanner having reception and transmission circuits to repeatedly scan a fetus within a mother's body with an ultrasonic wave via the ultrasonic probe and repeatedly acquire echo signals;
   an image generation unit configured to generate data of blood flow images based on the echo signals and to arrange the images according to heart beat time phase, a heart beat time phase of each image being estimated based upon changes over time in a form of the heart; and
   an interpolation processor configured to identify, using the arranged images, at least one pixel in which clutter components occupy the majority of the pixel value, and to interpolate a pixel value of the identified pixel based on pixel values of at least two other blood flow images corresponding to a substantially same cardiac phase and contiguous scanning timings as that of the blood flow image including the identified pixel.

2. The apparatus according to claim 1, wherein the processor specifies the pixel in which the clutter components occupy the majority of the pixel value by threshold processing.

3. The apparatus according to claim 2, wherein the interpolation processor localizes an interpolation target range to a region which has one of a volume and area with a value not less than a predetermined threshold and where a single lump is formed by a plurality of pixels in which the clutter components occupy the majority of a pixel value.

4. The apparatus according to claim 1, wherein the processor specifies, as the interpolation target blood flow image, a blood flow image having a region which has one of a volume and area with a value not less than a predetermined threshold and where a single lump is formed by a plurality of pixels in which the clutter components occupy the majority of a pixel value.

5. The apparatus according to claim 1, wherein the interpolation processor specifies, as the other blood flow images, a blood flow image corresponding to a cardiac cycle immediately before a cardiac cycle corresponding to the interpolation target blood flow image and a blood flow image corresponding to an immediately succeeding cardiac cycle.

6. The apparatus according to claim 1, wherein the interpolation processor divides the plurality of blood flow images into a plurality of groups in accordance with a plurality of cardiac phases, and executes interpolation processing in each group.

7. The apparatus according to claim 6, wherein the interpolation processor specifies, as the other blood flow images, a plurality of blood flow images at scanning timings immediately before and after the interpolation target blood flow image in each group.

8. The apparatus according to claim 7, wherein the interpolation processor specifies, as the other blood flow images, a blood flow image corresponding to a cardiac cycle immediately before the interpolation target blood flow image and a blood flow image corresponding to an immediately succeeding cardiac cycle.

9. The apparatus according to claim 1, further comprising an image creation generation unit configured to create a single blood flow image from a plurality of blood flow images including the interpolated blood flow image.

10. The apparatus according to claim 1, wherein
the ultrasonic scanner repeats scanning while changing a scanning position in the interior of the subject, and
the image generation unit generates a single blood flow image concerning an arbitrary cross section from a plurality of blood flow images including the interpolated blood flow image.

11. The apparatus according to claim 10, wherein the ultrasonic scanner repeats three-dimensional scanning for a three-dimensional region in the subject.

12. An ultrasonic diagnosis apparatus comprising:
an ultrasonic probe;
an ultrasonic scanner having reception and transmission circuits configured to repeatedly scan a fetus within a mother's body with an ultrasonic wave via the ultrasonic probe and repeatedly acquire echo signals;
an image generation unit configured to generate data of a plurality of blood flow images based on the echo signals and to arrange the images according to heart beat time phase, a heart beat time phase of each image being estimated based upon changes over time in a form of the heart; and
an interpolation processor configured to divide the plurality of arranged blood flow images into a plurality of groups in accordance with a plurality of cardiac phases, and executes interpolation processing for at least one pixel in which clutter components occupy the majority of a pixel value in each group.

13. The apparatus according to claim 12, wherein the interpolation processor specifies the pixel in which the clutter components occupy the majority of the pixel value by threshold processing.

14. The apparatus according to claim 13, wherein the interpolation processor localizes an interpolation target range to a region which has one of a volume and area with a value not less than a predetermined threshold and where a single lump is formed by a plurality of pixels in which the clutter components occupy the majority of a pixel value.

15. The apparatus according to claim 13, wherein the interpolation processor specifies, as the other blood flow images, a blood flow image corresponding to a cardiac cycle immediately before a cardiac cycle corresponding to the blood flow image including the at least one pixel in which the clutter components occupy the majority of the pixel value and a blood flow image corresponding to an immediately succeeding cardiac cycle.

16. The apparatus according to claim 13, further comprising an image creation unit configured to create a single blood flow image from a plurality of blood flow images including the interpolated blood flow image.

17. The apparatus according to claim 13, wherein
the ultrasonic scanner repeats scanning while changing a scanning position in the interior of the subject, and
the image generation unit generates a single blood flow image concerning an arbitrary cross section from a plurality of blood flow images including the interpolated blood flow image.

18. The apparatus according to claim 17, wherein the ultrasonic scanner repeats three-dimensional scanning for a three-dimensional region in the subject.

19. An ultrasonic diagnosis apparatus comprising:
an ultrasonic probe;
an ultrasonic scanner having reception and transmission circuits configured to repeatedly scan a fetus within a mother's body with an ultrasonic wave via the ultrasonic probe and repeatedly acquire echo signals;
an image generation unit configured to generate data of a plurality of images based on the echo signals and to arrange the images according to heart beat time phase, a heart beat time phase of each image being estimated based upon changes over time in a form of the heart;
an interpolation processor configured to divide the plurality of arranged images into a plurality of groups in accordance with a periodic motion phase of a specific part, and interpolates a specific image using images of immediately preceding and succeeding motion phases in each group; and
a display image generation unit configured to generate a single image from a plurality of images including the interpolated image.

* * * * *